United States Patent
Stein et al.

(10) Patent No.: US 6,727,395 B1
(45) Date of Patent: Apr. 27, 2004

(54) METHOD FOR PRODUCING HEXANEDIOL

(75) Inventors: Frank Stein, Bad Dürkheim (DE); Thomas Krug, Worms (DE); Thomas Nöbel, Limburgerhof (DE); Harald Rust, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 379 days.

(21) Appl. No.: 10/018,338
(22) PCT Filed: Jun. 21, 2000
(86) PCT No.: PCT/EP00/05739
§ 371 (c)(1), (2), (4) Date: Dec. 19, 2001
(87) PCT Pub. No.: WO01/02327
PCT Pub. Date: Jan. 11, 2001

(30) Foreign Application Priority Data

Jun. 30, 1999 (DE) .......................................... 199 29 831

(51) Int. Cl.$^7$ .......................... C07C 27/00; C07C 31/18; C07C 27/26
(52) U.S. Cl. ....................... 568/864; 568/852; 568/853; 568/854
(58) Field of Search ................................ 568/864, 852, 568/853, 854

(56) References Cited

U.S. PATENT DOCUMENTS 6,008,418 A    12/1999    Baur

FOREIGN PATENT DOCUMENTS

| EP | 673 909 | 9/1995 |
| WO | 97/31882 | 9/1997 |
| WO | 99/25672 | 3/1999 |

Primary Examiner—Samuel Barts
Assistant Examiner—Elvis O. Price
(74) Attorney, Agent, or Firm—Keil & Weinkauf

(57) ABSTRACT

A process for preparing 1,6-hexanediol from a carboxylic acid mixture comprising adipic acid, 6-hydroxycaproic acid and small amounts of 1,4-cyclohexanediols which is obtained as by-product in the oxidation of cyclohexane to cyclohexanone/cyclohexanol after water extraction of the reaction mixture followed by extraction with aqueous sodium hydroxide solution, by esterification of the acids and hydrogenation comprises a) liberating the carboxylic acids from the alkaline extract by addition of a mineral acid,
b) fractionating the organic phase comprising carboxylic acids to give a distillate comprising the low molecular weight monocarboxylic acids and a residue comprising adipic acid and 6-hydroxycaproic acid,
c) reacting the monocarboxylic an dicarboxylic acids present in the aqueous dicarboxylic acid mixture with a low molecular weight alcohol to give the corresponding carboxylic esters,
d) freeing the esterification mixture obtained of excess alcohol and low boilers in a first distillation step,
e) fractionating the bottom product in a second distillation step to give an ester fraction essentially free of 1,4-cyclohexanediols and a fraction comprising at least the major part of the 1,4-cyclohexanediols,
f) catalytically hydrogenating the ester fraction which is essentially free of 1,4-cyclohexanediols and
g) isolating 1,6-hexanediol from the hydrogenation product in a manner known per se in a final distillation step.

9 Claims, 2 Drawing Sheets

METHOD FOR PRODUCING HEXANEDIOL

This application is the national phase of PCT/EP00/05739, filed Jun. 21, 2000.

The present invention relates to a process for preparing 1,6-hexanediol which has a purity of at least 99% and is, in particular, essentially free of 1,4-cyclohexanediols from a carboxylic acid mixture obtained in the oxidation of cyclohexane to cyclohexanone/cyclohexanol using oxygen or oxygen-containing gases after water extraction of the reaction mixture followed by extraction with aqueous sodium hydroxide solution, which comprises neutralization of the extract, fractionation of the organic phase into a low boiler fraction and a high boiler fraction, esterification of the latter, fractionation of the esterification mixture to give an ester fraction which is free of 1,4-cyclohexanediols, hydrogenation of this ester fraction and purification of the 1,6-hexanediol by distillation. EP-A 883 590 discloses a process for preparing 1,6-hexanediol from a carboxylic acid mixture comprising adipic acid, 6-hydroxycaproic acid and small amounts of 1,4-cyclohexanediols which is obtained as by-product in the oxidation of cyclohexane to cyclohexanone/cyclohexanol using oxygen or oxygen-containing gases after water extraction of the reaction mixture, by esterification of the acids and hydrogenation, in which a) the monocarboxylic and dicarboxylic acids present in the aqueous dicarboxylic acid mixture are reacted with a low molecular weight alcohol to give the corresponding carboxylic esters, b) the esterification mixture obtained is freed of excess alcohol and low boilers in a first distillation step, c) the bottom product is, in a second distillation step, fractionated to give an ester fraction essentially free of 1,4-cyclohexanediols and a fraction comprising at least the major part of the 1,4-cyclohexanediols, d) the ester fraction which is essentially free of 1,4-cyclohexanediols is catalytically hydrogenated and e) 1,6-hexanediol is isolated from the hydrogenation product in a manner known per se in a final distillation step.

The aqueous solutions of carboxylic acids employed as starting material in this process are formed as by-products in the oxidation of cyclohexane to cyclohexanol and cyclohexanone (cf. Ullmann's Encyclopedia of Industrial Chemistry, 5. Ed, 1987, Vol. A8, pp. 2/9); they will hereinafter be referred to as dicarboxylic acid solution (DCS). They generally comprise (calculated on an anhydrous basis in % by weight) from 10 to 40% of adipic acid, from 10 to 40% of 6-hydroxycaproic acid, from 1 to 10% of glutaric acid, from 1 to 10% of 5-hydroxyvaleric acid, from 1 to 5% of 1,2-cyclohexanediols (cis and trans), from 1 to 5% of 1,4-cyclohexanediol (cis and trans), from 2 to 10% of formic acid and also many further monocarboxylic and dicarboxylic acids, esters, oxo and oxa compounds whose individual contents generally do not exceed 5%. Examples which may be mentioned are acetic acid, propionic acid, butyric acid, valeric acid, caproic acid, oxalic acid, malonic acid, succinic acid, 4-hydroxybutyric acid and gamma-butyrolactone.

The water scrub is generally followed by a further scrub using aqueous sodium hydroxide solution which gives a waste stream consisting of an alkaline solution of salts of a large number of different carboxylic acids, known as "caustic water".

The formation of this stream is described in Ullmann's Encyclopedia of Industrial Chemistry, 5th Ed. 1987, Vol. A, p. 219.

In contrast to the DCS which predominantly comprises readily water-soluble acids such as dicarboxylic acids, hydroxycarboxylic acids and diols, this caustic water stream comprises mostly less polar carboxylic acids, e.g. linear unsubstituted monocarboxylic acids and, in much smaller amounts, $C_6$ building blocks such as adipic acid and hydroxycaproic acid. Since there has up to now been no known economic use of the caustic water, it has to be disposed of. This is achieved in Europe by incineration of the salts to form "heavy soda" ($Na_2CO_3$). In the USA, disposal is also carried out by means of "deep welling", i.e. injection into deep geological layers. The latter is undesirable from an ecological point of view and in view of the rule of sustainability.

It is an object of the present invention to find a better use for the caustic water so as to obtain a useful product.

We have found that this object is achieved by using the caustic water for preparing 1,6-hexanediol by the process of EP-A 883 590 when the carboxylic acids present in the alkaline extract are liberated by addition of a mineral acid, preferably sulfuric acid, the organic phase is separated off and separated into a low boiler fraction consisting essentially of the monocarboxylic acids and a high boiler fraction comprising about 30% of $C_6$-dicarboxylic acids and 6-hydroxycaproic acid, and this fraction is processed further by the process described.

DETAILED DESCRIPTION OF THE INVENTION

Figure 1:
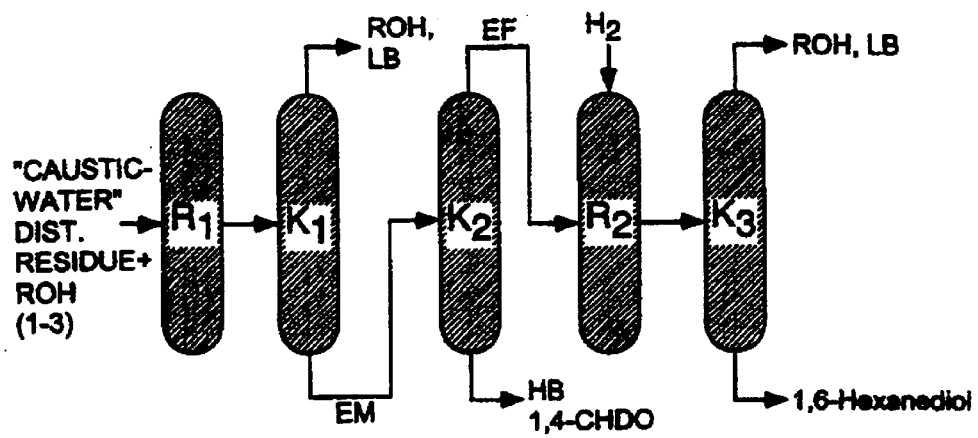
FIG. 1 is a schematic representation of variant A of the invention.

The present invention accordingly provides a process for preparing 1,6-hexanediol from a carboxylic acid mixture comprising adipic acid, 6-hydroxycaproic acid and small amounts of 1,4-cyclohexanediols which is obtained as by-product in the oxidation of cyclohexane to cyclohexanone/cyclohexanol using oxygen or oxygen-containing gases after water extraction of the reaction mixture followed by extraction with aqueous sodium hydroxide solution, by esterification of the acids and hydrogenation, which comprises a) liberating the carboxylic acids from the alkaline extract by addition of a mineral acid, b) fractionating the organic phase comprising the carboxylic acids to give a distillate comprising low molecular weight monocarboxylic acids and a residue comprising adipic acid as main constituent, c) reacting the residue comprising adipic acid and 6-hydroxycaproic acid with a low molecular weight alcohol to give a mixture of carboxylic esters, d) freeing the esterification mixture obtained of excess alcohol and low boilers in a first distillation step, e) fractionating the bottom product in a second distillation step to give an ester fraction essentially free of 1,4-cyclohexanediols and a fraction comprising at least the major part of the 1,4-cyclohexanediols, f) catalytically hydrogenating the ester fraction which is essentially free of 1,4-cyclohexanediols and g) isolating 1,6-hexanediol from the hydrogenation product in a manner known per se in a final distillation step.

The success of this process was surprising since the amount of starting acids which can form hexanediol, i.e. in the high boiler fraction serving as starting material, present in the caustic water is only about 30% by weight and a huge number of further acids (several hundred) are also present in an amount of about 70% and it is nevertheless possible to successfully prepare highly pure hexanediol.

Table 1 below shows representative compositions of DCS and caustic water after sulfur acid treatment.

TABLE 1

|  | DCS average composition | Caustic water average composition |
|---|---|---|
| Water content [% by weight] | 49 | 19.9 |
| $C_6$ content |  |  |
| Adipic acid [% by weight] | 16 | 4.0 |
| Hydroxycaproic acid [% by weight] | 14 | 9.2 |
| $C_6$ content (total) [% by weight] | 59 (anhydrous basis) | 31 (anhydrous basis) |
| $C_5$ content (% by weight] | 2.8 | 2.6 |
| Formic acid [% by weight] | 2.5 | 1.2 |
| $C_2$-Monocarboxylic acids (% by weight] | 0.4 | 1.2 |
| $C_3$-Monocarboxylic acids (% by weight] | <0.1 | 1.0 |
| $C_4$-Monocarboxylic acids [% by weight] | 1.6 | 2.7 |
| $C_5$-Monocarboxylic acids [% by weight] | 0.4 | 19.5 |
| $C_6$-Monocarboxylic acids [% by weight] | <0.1 | 11.8 |
| Monocarboxylic acids (total) [% by weight] | <5.1 | 37.4 |
| Cyclohexanediols [% by weight] | 1.0 | 1.3 |
| High boilers [% by weight] | 12.1 | 25.8 |
| Total | 100 | 100 |

The removal of the low-boiling components (water, monocarboxylic acids) by distillation enables the content of desired $C_6$ components to be increased to about 32%. The removal of the low-boiling components by distillation is carried out in a manner known per se at subatmospheric pressure in columns. The column packing used is, for example, structured fabric packing or loose packing elements.

The results of a representative distillation are shown in Table 2, and the composition of the fractions is shown in Table 3.

TABLE 2

|  | Bottom temperature [° C.] | Top temperature [° C.] | Pressure [mbar] | Amount [g] |
|---|---|---|---|---|
| Amount of feed |  |  |  | 349 |
| Fraction 1 | 24–50 | 21–24 | <1 | 30 |
| Fraction 2 | 50–105 | 24–62 | <1 | 92 |
| Cold trap |  |  |  | 44 |
| Residue |  |  |  | 165 |

TABLE 3

|  | Low boilers Fraction 1 + Fraction 2 + cold trap | Residue |
|---|---|---|
| $C_6$ content |  |  |
| Adipic acid [% by weight] | 0 | 8.2 |
| Hydroxycaproic acid [% by weight] | 0 | 18.5 |
| CE content (total) [% by weight] | 0 | 32.2 |
| Formic acid [% by weight] | 1.8 | 0.7 |
| $C_2$-Monocarboxylic acids (% by weight] | 2.3 | 0.2 |
| $C_3$-Monocarboxylic acids (% by weight] | 2.0 | 0.2 |
| $C_4$-Monocarboxylic acids [% by weight] | 5.4 | 0.3 |
| $C_5$-Monocarboxylic acids [% by weight] | 33.0 | 6.2 |
| $C_6$-Monocarboxylic acids [% by weight] | 10.6 | 9.8 |
| Monocarboxylic acids (total) [% by weight] | 55.1 | 17.4 |

The procedure in steps (a) and (b) for obtaining the starting materials for the esterification (c) is generally as follows:

To convert the sodium carboxylates present in the caustic water into the corresponding carboxylic acids, the caustic water is treated with mineral acids (preferably sulfuric acid) while stirring until the pH is less than 7.

The liberation of the carboxylic acids from their Na salts results in formation of an organic phase which is separated from the aqueous phase and worked up further. The aqueous phase is discarded.

In a subsequent column, the organic phase is fractionated so as to give water and $C_1$–$C_6$ monocarboxylic acids at the top and hydroxycarboxylic and dicarboxylic acids at the bottom.

The esterification (c) can be carried out without addition of catalysts, but is preferably carried out in the presence of catalysts. As low molecular weight alcohols, use is generally made of those having from 1 to 10 carbon atoms, in particular alkanols having from 1 to 8 carbon atoms. Diols such as butanediol or pentanediol are also suitable in principle.

The industrially preferred alcohols for the esterification are n-or i-butanol and, in particular, methanol.

In the case of the esterification using methanol (variant A), the procedure is to take off a methyl carboxylate fraction which is essentially free of 1,4-cyclohexanediols at the top of the column and obtain a bottom fraction comprising the high boilers and the 1,4-cyclohexanediols in the distillation step (e), and to hydrogenate the methyl carboxylate fraction catalytically in the hydrogenation step (f).

If n- or i-butanol is used for the esterification (variant B), the 1,4-cyclohexanediols together with the low boilers are taken off at the top of the column in the distillation step (e) and the butyl carboxylates are obtained at a side offtake or as bottoms comprising them and are subsequently introduced into the hydrogenation step (f).

BRIEF DESCRIPTION OF THE DRAWINGS

The process of the present invention and its variants A (FIG. 1) and B (FIG. 2) are described in general terms below (where the terms "at the top" and "as bottoms" refer to the stream being taken off above and below the feed point, respectively):

Variant A

As shown in FIG. 1, the residue comprising adipic acid and 6-hydroxycaproic acid from step (b) is fed together with a $C_1$- to $C_3$-alcohol, preferably methanol, into the esterification reactor $R_1$ in which the carboxylic acids are esterified. The esterification mixture obtained then goes to column $K_1$, in which the excess alcohol (ROH), water and low boilers (LB) are distilled off at the top and the ester mixture (EM) is taken off as bottoms and fed into the fractionation column $K_2$. In this column, the mixture is fractionated to give an ester fraction (EF) which is essentially free of 1,4-cyclohexanediols and a bottom fraction comprising high boilers (HB) and 1,4-cyclohexanediols (1,4–CHDO). The ester fraction (EF) is then catalytically hydrogenated in the hydrogenation reactor $R_2$ and the hydrogenation mixture is fractionated in the distillation column $K_3$ to give alcohol (ROH), low boilers (LB) and pure 1,6-hexanediol.

Variant B

Figure 2:
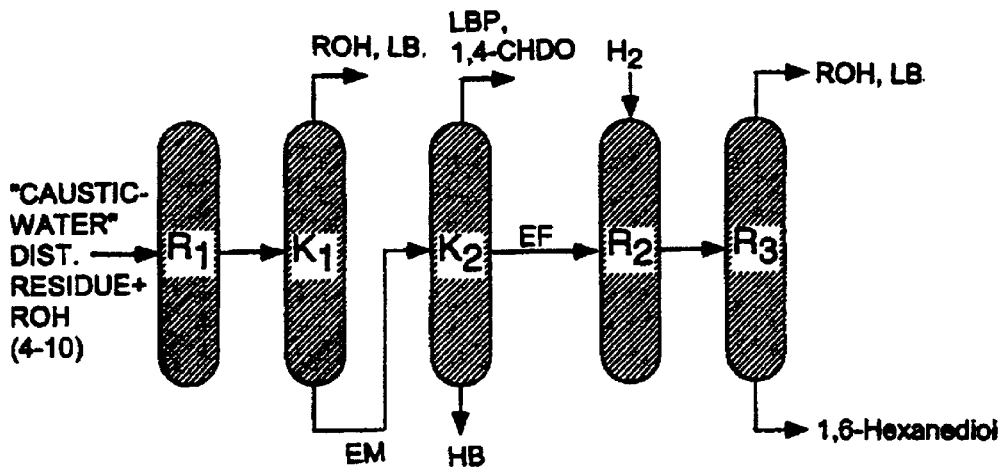
FIG. 2 is a schematic representation of variant B of the invention where an ester fraction is obtained as a side fraction of column K2.

If alcohols having 4 or more carbon atoms, in particular n- or i-butanol, are used for the esterification, the process shown in FIG. 2 differs from that described above only in that the ester mixture (EM) is fractionated in the fractionation column $K_2$ to give a low-boiling top product (LBP) comprising the 1,4-cyclohexanediols (1,4–CHDO) and an ester fraction (EF) which is essentially free of 1,4-cyclohexanediol and is obtained as a side fraction or as bottoms comprising the ester fraction and is fed to the hydrogenation step ($R_2$).

Figure 3:
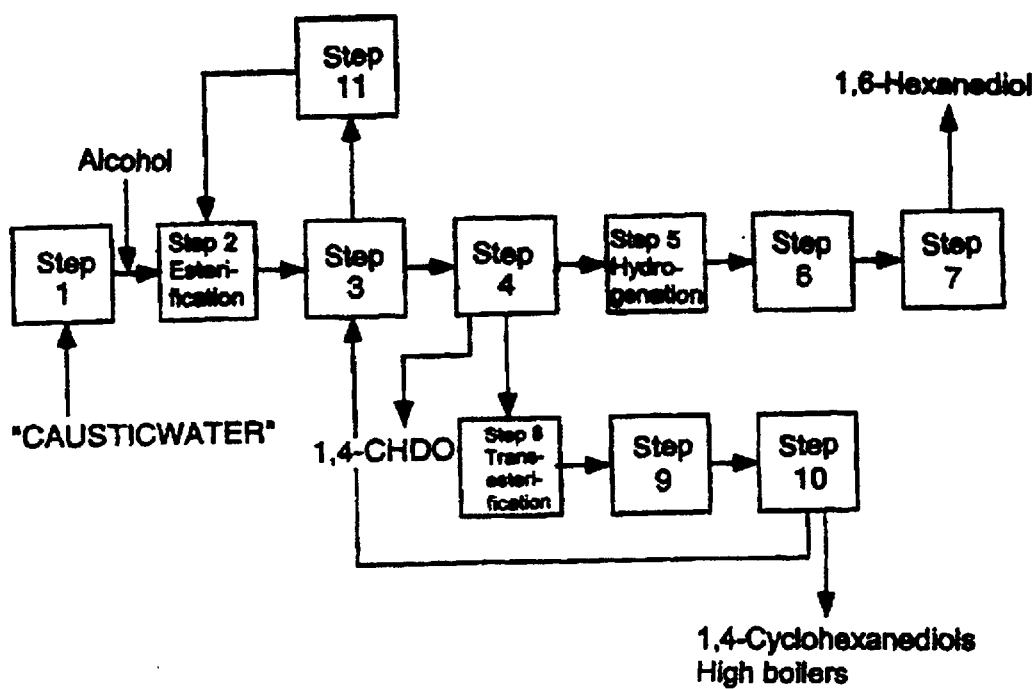
FIG. 3 is a more detailed schematic representation of the invention where the individual process steps are broken down into further steps.

The process of the present invention is explained in more detail as follows. In FIG. 3, the individual process steps are broken down into further steps, where the steps 2, 3, 4, 5, 6, 7 are essential to the process and the steps 3 and 4 or 6 and 7 may be combined. The steps 8, 9, 10 and 11 are optional, but may be useful for improving the economics of the process.

In step 1, as already described, a distillate and a distillation residue are obtained from the caustic water by acidifying with mineral acid, separating off the organic phase comprising the carboxylic acids and fractionating the carboxylic acid mixture. The distillation residue is then fed to the esterification step 2.

An alcohol having from 1 to 10 carbon atoms, in variant A an alcohol having from 1 to 3 carbon atoms, i.e. methanol, ethanol, propanol or isopropanol, preferably methanol, and in variant B an alcohol having from 4 to 10, in particular from 4 to 8, carbon atoms, particularly preferably n-butanol, isobutanol, n-pentanol or i-pentanol, is mixed into the carboxylic acid stream from step 1.

The mixing ratio of alcohol to carboxylic acid stream (mass ratio) can be from 0.1 to 30, preferably from 0.2 to 20, particularly preferably from 0.5 to 10.

This mixture enters, as melt or solution, the reactor of step 2 in which the carboxylic acids are esterified with the alcohol. The esterification reaction can be carried out at from 50 to 400° C., preferably from 70 to 300° C., particularly preferably-from 90 to 200° C. An external pressure can be applied, but the esterification is preferably carried out under the autogenous pressure of the reaction system. As esterification apparatus, it is possible to use a stirred reactor or a flow tube or a plurality of each of these. The residence time necessary for the esterification is from 0.3 to 10 hours, preferably from 0.5 to 5 hours. The esterification reaction can proceed without addition of the catalyst, but a catalyst is preferably added to increase the reaction rate. This can be a homogeneously dissolved catalyst or a solid catalyst. Examples of homogeneous catalysts are sulfuric acid, phosphoric acid, hydrochloric acid, sulfonic acids such as p-toluenesulfonic acid, heteropolyacids such as tungstophosphoric acid or Lewis acids such as aluminum, vanadium, titanium or boron compounds. Preference is given to mineral acids, in particular sulfuric acid. The weight ratio of homogeneous catalyst to carboxylic acid melt is generally from 0.0001 to 0.5, preferably from 0.001 to 0.3.

Suitable solid catalysts are acid or superacid materials, e.g. acid and superacid metal oxides such as $SiO_2$, $Al_2O_3$, $SnO_2$, $ZrO_2$ or sheet silicates or zeolites, which may all be doped with mineral acid anions such as sulfate or phosphate to increase the acid strength, or organic ion exchangers having sulfonic acid or carboxylic acid groups. The solid catalysts can be arranged as a fixed bed or be used as a suspension.

The water formed in the reaction is advantageously removed continuously, e.g. by means of a membrane or by distillation.

The completeness of the reaction of the free carboxyl groups present in the carboxylic acid melt is determined by means of the acid number (mg KOH/g) measured after the reaction. It is, after subtraction of any acid added as catalyst, from 0.01 to 50, preferably from 0.1 to 10. At these values, not all carboxyl groups present in the system are in the form of esters of the alcohol used, but part may be in the form of dimeric or oligomeric esters, e.g. with the OH end of the hydroxycaproic acid.

The esterification mixture is fed to step 3, a membrane system or preferably a distillation column. If a dissolved acid has been used as catalyst for the esterification reaction, the esterification mixture is advantageously neutralized with a base, with from 1 to 1.5 base equivalents being added per acid equivalent of catalyst. Bases used are, as a rule, alkali metal or alkaline earth metal oxides, carbonates, hydroxides or alkoxides, or amines, either as such or dissolved in the esterification alcohol.

If a column is used in step 3, the feed stream is preferably introduced into the column between the top and bottom streams. At the top, the excess esterification alcohol ROH, water and, for example, the corresponding esters of formic acid, acetic acid and propionic acid are taken off at pressures of from 1 to 1500 mbar, preferably from 20 to 1000 mbar, particularly preferably from 40 to 800 mbar, and temperatures of from 0 to 150° C., preferably from 15 to 90° C., and in particular from 25 to 75° C. This stream can either be incinerated or, preferably, worked up further in step 11.

The bottom fraction obtained is an ester mixture consisting predominantly of the esters of the alcohol ROH used with dicarboxylic acids such as adipic acid and glutaric acid, hydroxycarboxylic acids such as 6-hydroxycaproic acid and 5-hydroxyvaleric acid and also oligomers and free or esterified 1,4-cyclohexanediols. It may be useful to permit a residual content of water and/or alcohol ROH of up to 10% by weight in the ester mixture. The bottom temperatures are from 70 to 250° C., preferably from 80 to 220° C., particularly preferably from 100 to 190° C.

The stream from step 3 which has largely been freed of water and esterification alcohol ROH is fed to step 4. This is a distillation column at which the feed point is generally between the low-boiling components and the high-boiling components. The column is operated at temperatures of from 10 to 300° C., preferably from 20 to 270° C., particularly preferably from 30 to 250° C., and pressures of from 1 to 1000 mbar, preferably from 5 to 500 mbar, particularly preferably from 10 to 200 mbar.

In variant A, i.e. esterification using $C_1$–$C_3$-alcohols, in particular methanol, the stream from step 3 is then separated into a top fraction to be hydrogenated and a bottom fraction comprising the 1,4-cyclohexanediols.

The top fraction consists predominantly of residual water and residual alcohol ROH, esters of the alcohol ROH with monocarboxylic acids, predominantly $C_3$–$C_6$-monocarboxylic acids, esters of hydroxycarboxylic acids such as 6-hydroxycaproic acid and 5-hydroxyvaleric acid, and also, especially, the diesters of dicarboxylic acids such as adipic acid, glutaric acid and succinic acid, also 1,2-cyclohexanediols, caprolactone and valerolactone.

The components mentioned can be separated off together at the top and introduced into the hydrogenation (step 5) or, in a further preferred embodiment, separated in the column into a top stream comprising predominantly residual water and residual alcohol and the abovementioned esters of $C_3$–$C_5$-carboxylic acids and a side stream comprising predominantly the abovementioned esters of $C_6$-carboxylic acids and dicarboxylic acids which then go to the hydrogenation.

The high-boiling components of the stream from step 4, consisting predominantly of 1,4-cyclohexanediols or their esters, dimeric or oligomeric esters and possibly polymeric constituents of the DCL which are not defined in more detail, are separated off via the stripping section of the column. These can be obtained together or predominantly the 1,4-cyclohexanediols can be separated off via a side stream from the column in the stripping section and the remainder can be separated off at the bottom. The 1,4-cyclohexanediols obtained in this way can be used, for example, as starting material for active compounds. The high-boiling components with or without the 1,4-cyclohexanediols can either be incinerated or, in a preferred embodiment, go to the transesterification in step 8.

In variant B, i.e. the esterification using $C_4$–$C_{10}$-alcohols, in particular n- or i-butanol, the stream from step 3 can be fractionated in step 4 to give a top fraction comprising the 1,4-cyclohexanediols, a side stream comprising predominantly the $C_6$-esters which goes to the hydrogenation and a bottom stream comprising high boilers which can, if desired, go to step 8.

The top fraction consists predominantly of residual alcohol ROH, $C_1$–$C_3$-monoesters of the alcohol ROH, valerolactone and 1,2- and 1,4-cyclohexanediols.

The side stream comprises predominantly diesters of succinic acid, glutaric acid and adipic acid and also monoesters of 5-hydroxyvaleric acid and 6-hydroxycaproic acid. This side stream can be taken off either above or below the feed point to the column and be introduced into the hydrogenation (step 5).

The bottom stream comprising oligomeric esters and other high boilers can, similarly to variant A, either be incinerated or advantageously go to step 8.

In a further embodiment, the $C_6$-esters are, in step 4, either separated off together with the bottom stream and then, in a further column, separated as bottom product from the above-described top fraction which consists predominantly of residual alcohol ROH, $C_1$–$C_3$-monoesters of the alcohol ROH, valerolactone and 1,2- and 1,4-cyclohexanediols, or are separated as a top stream from the high boilers.

The fraction from step 4 which is free or virtually free of 1,4-cyclohexanediols, either the total stream or the side stream comprising mainly esters of $C_6$ acids, is introduced into the hydrogenation step 5.

Steps 3 and 4 can, particularly when only small amounts are being dealt with, be combined. For this purpose, for example, the $C_6$-ester stream can be obtained in a batchwise fractional distillation, again without 1,4-cyclohexanediols getting into the stream passed to the hydrogenation step.

The hydrogenation is carried out catalytically either in the gas phase or the liquid phase. As catalysts, it is in principle possible to use all homogeneous and heterogeneous catalysts suitable for the hydrogenation of carbonyl groups, for example metals, metal oxides, metal compounds or mixtures thereof. Examples of homogeneous catalysts are described, for example, in Houben-Weyl, Methoden der Organischen Chemie, Volume IV/1c, Georg Thieme Verlag Stuttgart, 1980, pp. 45–67, and examples of heterogeneous catalysts are described, for example, in Houben-Weyl, Methoden der Organischen Chemie, Volume IV/1c, pp. 16–26.

Preference is given to using catalysts which comprise one or more of the elements of transition groups I and VI to VIII of the Periodic Table of the Elements, preferably copper, chromium, molybdenum, manganese, rhenium, ruthenium, cobalt, nickel and palladium, particularly preferably copper, cobalt or rhenium.

The catalysts can consist entirely of the active components or the active components can be applied to supports. Suitable support materials are, for example, $Cr_2O_3$, $Al_2O_3$, $SiO_2$, $ZrO_2$, $ZnO_2$, BaO and MgO or mixtures thereof.

Preference is given to using heterogeneous catalysts which are either arranged as a fixed bed or are used as a suspension. If the hydrogenation is carried out in the gas phase over a fixed-bed catalyst, temperatures of from 150 to 300° C. and pressures of from 1 to 50 bar are generally employed. At least that amount of hydrogen necessary for starting materials, intermediates and products never to become liquid during the reaction is used as hydrogenating agent and carrier gas.

If the hydrogenation is carried out in the liquid phase using a fixed-bed or suspended catalyst, it is generally carried out at temperatures of from 100 to 350° C., preferably from 120 to 300° C., and pressures of from 30 to 350 bar, preferably from 40 to 300 bar.

The hydrogenation can be carried out in one reactor or in a plurality of reactors connected in series. The hydrogenation in the liquid phase over a fixed bed can be carried out in either the downflow mode or the upflow mode. In a preferred embodiment, use is made of a plurality of reactors and the major part of the esters is hydrogenated in the first reactor and the first reactor is preferably operated using a liquid circuit to remove heat and the downstream reactor or reactors are preferably operated without circulation to complete the conversion.

The hydrogenation can be carried out batchwise, but is preferably carried out continuously.

The hydrogenation product consists essentially of 1,6-hexanediol and the alcohol ROH. Further constituents are, especially if the total low-boiling stream from step 4 has been used as per variant A, 1,5-pentanediol, 1,4-butanediol, 1,2-cyclohexanediols and also small amounts of monoalcohols having from 1 to 6 carbon atoms and water.

In step 6, which is, for example, a membrane system or preferably a distillation column, this hydrogenation product is fractionated to give the alcohol ROH which further comprises the major part of the further low-boiling components and a stream comprising predominantly 1,6-hexanediol together with 1,5-pentanediol and the 1,2-cyclohexanediols. Here, top temperatures of from 0 to 120° C., preferably from 20 to 100° C., particularly preferably from 30 to 90° C., and bottom temperatures of from 100 to 270° C., preferably from 140 to 260° C., particularly preferably from 160 to 250° C., are set at a pressure of from 10 to 1500 mbar, preferably from 30 to 1200 mbar, particularly preferably from 50 to 1000 mbar. The low-boiling stream can either be returned directly to the esterification of step 2 or can go to step 8 or to step 11.

The 1,6-hexanediol-containing stream is purified in a column in step 7. Here, 1,5-pentanediol, any 1,2-cyclohexanediols and also any further low boilers present are separated off at the top. If the 1,2-cyclohexanediols and/or 1,5-pentanediol are to be isolated as additional products of value, this top product can be fractionated in a further column. At the bottom, any high boilers present are discharged. 1,6-hexanediol having a purity of at least 99% is taken from the column as a side stream. Here, top temperatures of from 50 to 200° C., preferably from 60 to 150° C., and bottom temperatures of from 130 to 270° C., preferably from 150 to 250° C., are set at pressures of from 1 to 1000 mbar, preferably from 5 to 800 mbar, particularly preferably from 20 to 500 mbar.

If only relatively small amounts of 1,6-hexanediol are to be prepared, steps 6 and 7 can also be combined in a batchwise fractional distillation.

In order to carry out the process of the present invention as economically as possible, it is useful to recover the esterification alcohol ROH and to reuse it for the esterification. For this purpose, the stream from step 3 and/or 6 comprising predominantly the alcohol ROH, for example methanol, can be worked up in step 11. In step 11, use is advantageously made of a column in which the components having boiling points lower than the alcohol ROH are taken off at the top and water and components having boiling points higher than that of the alcohol ROH are separated as bottoms from the alcohol ROH which is obtained as a side stream. The column is advantageously operated at from 500 to 5000 mbar, preferably from 800 to 3000 mbar.

In a further preferred embodiment of the process of the present invention, the high-boiling stream from step 4 (in variant A) is used to increase the total yield of 1,6-hexanediol based on adipic acid and 6-hydroxycaproic acid used. For this purpose, the dimeric and oligomeric esters of adipic acid and hydroxycaproic acid are reacted in step 8 with further amounts of the alcohol ROH in the presence of a catalyst. The weight ratio of alcohol ROH and the bottom stream from step 4 is from 0.1 to 20, preferably from 0.5 to 10, particularly preferably from 1 to 5.

Suitable catalysts are in principle those described above for the esterification in step 2. However, preference is given to using Lewis acids. Examples of these are compounds or complexes of aluminum, tin, antimony, zirconium or titanium, for example zirconium acetylacetonate or tetraalkyl titanates, e.g. tetraisopropyl titanate, which are employed in concentrations of from 1 to 10000 ppm, preferably from 50 to 6000 ppm, particularly preferably from 100 to 4000 ppm, based on the transesterification mixture. Particular preference is here given to titanium compounds.

The transesterification can be carried out batchwise or continuously, in one reactor or a plurality of reactors, in stirred vessels or tube reactors connected in series, at temperatures of from 100 to 300° C., preferably from 120 to 270° C., particularly preferably from 140 to 240° C., and autogenous pressure. The residence times necessary are from 0.5 to 10 hours, preferably from 1 to 4 hours.

In the case of the esterification using methanol, this stream from step 8 can, for example, be returned to step 3. To avoid accumulation of high boilers, especially 1,4-cyclohexanediols, a substream of the high boilers from step 4 then has to be bled off discontinuously or continuously. A further possibility is not to return the stream from step 8 to step 3 but to fractionate it, using a method analogous to step 3, in a step 9 to give predominantly alcohol ROH, which can then go either to step 2, step 8 or step 11, and a stream comprising the esters.

This ester stream can in principle (with the proviso of avoiding accumulations of the 1,4-cyclohexanediols) be returned to step 4 or is preferably fractionated in a further step 10 into the esters of the $C_6$ acids and, somewhat insignificant in terms of quantity, firstly the esters of the $C_5$ acids, which can be introduced either into step 4 or directly into step 5, and secondly high boilers comprising the 1,4-cyclohexanediols, after which the high boilers are discharged.

This makes it possible to achieve 1,6-hexanediol yields of more than 95%, and purities of over 99%.

The novel process thus allows highly pure 1,6-hexanediol to be obtained in high yield from a waste product in an economical manner.

The process is illustrated by the following example but is not restricted thereby.

Example (Variant A)

Step 1:

21 kg of caustic water were admixed with concentrated sulfuric acid until a pH of 1 had been reached; this resulted in formation of an organic phase.

The organic phase was fractionally distilled in a 50 cm packed column (1 mbar; 20–65° C. at the top, up to 110° C. at the bottom).

The low boilers obtained (6.1 kg) comprised mainly water and $C_1$–$C_6$-monocarboxylic acids. The bottoms (5.5 kg) comprised virtually the total amount of adipic acid and hydroxycaproic acid.

Step 2 (Esterification):

5.5 kg/h of the bottom stream from step 1 were reacted continuously with 8.3 kg/h of methanol and 14 g/h of sulfuric acid in a tube reactor (1=0.7 m, diam.=1.8 cm, residence time=2.7 h). The acid number of the product minus sulfuric acid was about 10 mg KOH/g.

Step 3 (Removal of excess alcohol and of water):

The esterification stream from step 2 was distilled in a 20 cm packed column (1015 mbar, 65° C. at the top, up to 125° C. at the bottom). 7.0 kg were taken off at the top and 6.8 kg were obtained as bottom product.

Step 4 (Fractionation; 1,4-cyclohexanediol removal):

The bottom stream from step 3 was fractionally distilled in a 50 cm packed column (1 mbar, 70–90° C. at the top, up to 180° C. at the bottom). The bottoms (1.9 kg) comprised virtually all 1,4-cyclohexanediols.

0.6 kg of low boilers were distilled off (1,2-cyclohexanediols, valerolactone, methyl 5-hydroxyvalerate, dimethyl glutarate, dimethyl succinate, etc.). 4.3 kg of a fraction comprising predominantly dimethyl adipate and methyl 6-hydroxycaproate were obtained.

The top stream, which represents the ester fraction, was passed to the hydrogenation step 5.

Step 5 (Hydrogenation):

4.3 kg of the $C_6$-ester fraction from step 4 were hydrogenated continuously in a 25 ml reactor over a catalyst (catalyst, 70% by weight of CuO, 25% by weight of ZnO, 5% by weight of $Al_2O_3$) which had been activated beforehand at 180° C. in a stream of hydrogen. The feed rate was 20 g/h, the pressure was 220 bar and the temperature was 220° C. The ester conversion was 99.5% and the 1,6-hexanediol selectivity was over 99%.

Steps 6 and 7:

4.0 kg of the hydrogenation product from step 5 were fractionally distilled (distillation pot with superposed 70 cm packed column, reflux ratio=2). At 1013 mbar, 1 kg of methanol was distilled off. After application of a vacuum (20 mbar), predominantly the 1,2-cyclohexanediols and 1,5-pentanediol distilled off.

Subsequently (b.p.=146° C.), 1,6-hexanediol having a purity of 99.8% distilled off. (Balance predominantly 1,5-pentanediol.)

Step 8:

1.9 kg of the bottom product from step 4 were admixed with 3.8 kg of methanol and 3.8 g of tetra-i-propyl titanate and reacted continuously in a 1 m long, 440 ml capacity tube reactor filled with 3 mm V2A rings. The mean residence time was about 2 hours.

Step 9:

The product from step 8 was fractionally distilled in an apparatus analogous to that described in step 3. At a top temperature of 65° C., 3.5 kg were distilled off (predominantly methanol) 2.2 kg remained in the bottoms.

Step 10:

The bottoms from step 9 were, using a method analogous to step 4, fractionally distilled to a bottom temperature of 160° C. This gave 1.3 kg of distillate which can be hydrogenated directly or returned to step 4. Composition: 52% of methyl 6-hydroxycaproate, 31% of dimethyl adipate, 5% of dimethyl glutarate, 4% of methyl 5-hydroxycaproate and many further components which are insignificant in terms of quantity.

Step 11:

7 kg of the top product from step 3 were fractionally distilled at 1015 mbar in a 20 cm packed column. This gave, at a top temperature of 59–65° C., 0.8 kg of a first fraction comprising predominantly methanol together with $C_1$–$C_4$-monomethyl esters. At a top temperature of 65° C., 5.6 kg of methanol having a purity of >99% were obtained. The bottoms (0.6 kg) consisted predominantly of water.

We claim:

1. A process for preparing 1,6-hexanediol from a carboxylic acid mixture comprising adipic acid, 6-hydroxycaproic acid and small amounts of 1,4-cyclohexanediols which is obtained as by-product in the oxidation of cyclohexane to cyclohexanone/cyclohexanol using oxygen or oxygen-containing gases after water extraction of the reaction mixture followed by extraction with aqueous sodium hydroxide solution, by esterification of the acids and hydrogenation, which comprises a) liberating the carboxylic acids from the alkaline extract by addition of a mineral acid, b) fractionating the organic phase comprising low molecular weight carboxylic acids to give a distillate comprising the monocarboxylic acids and a residue comprising adipic acid, c) reacting the residue comprising adipic acid and hydroxycaproic acid with a low molecular weight alcohol to give the corresponding carboxylic esters, d) freeing the esterification mixture obtained of excess alcohol and low boilers in a first distillation step, e) fractionating the bottom product in a second distillation step to give an ester fraction essentially free of 1,4-cyclohexanediols and a fraction comprising at least the major part of the 1,4-cyclohexanediols, f) catalytically hydrogenating the ester fraction which is essentially free of 1,4-cyclohexanediols and g) isolating 1,6-hexanediol from the hydrogenation product in a manner known per se in a final distillation step.

2. A process as claimed in claim 1, wherein the carboxylic acid mixture is dewatered prior to the esterification.

3. A process as claimed in claim 1, wherein the esterification is carried out using alkanols having from 1 to 3 carbon atoms.

4. A process as claimed in claim 1, wherein the esterification is carried out using alkanols having from 4 to 10 carbon atoms.

5. A process as claimed in claim 1, wherein the esterification is carried out using methanol and, in the distillation step (e), a methyl carboxylate fraction which is essentially free of 1,4-cyclohexanediols is obtained at the top of the column and a fraction comprising the high boilers and the 1,4-cyclohexanediols is obtained at the bottom, and the methyl carboxylate fraction is catalytically hydrogenated in the hydrogenation step (f).

6. A process as claimed in claim 1, wherein the esterification is carried out using n- or i-butanol and, in the distillation step (e), the 1,4-cyclohexanediols together with the low boilers are taken off at the top and the butyl carboxylates are obtained at a side offtake or as bottoms comprising them and are catalytically hydrogenated in the hydrogenation step (f).

7. A process as claimed in claim 1, wherein the alcohol is isolated in pure form from the top product of the distillation step (d) comprising unreacted alcohol and is returned to the esterification step (e).

8. A process as claimed in claim 1, wherein at least part of the bottom product from step (e) is subjected to renewed esterification with further addition of the low molecular weight alcohol and an esterification catalyst and is fractionated in a separate distillation step in a manner analogous to (d) and (e), or the renewed esterification is carried out only after removal of the 1,4-cyclohexanediols, and the fraction comprising the carboxylic esters is introduced into the hydrogenation step (f).

9. A process as claimed in claim 1, wherein the hydrogenation is carried out using catalysts which comprise copper, cobalt and/or rhenium as catalytically active main constituents.

* * * * *